(12) United States Patent
Alley et al.

(10) Patent No.: US 7,448,407 B2
(45) Date of Patent: Nov. 11, 2008

(54) LATCHED VALVE ASSEMBLY

(75) Inventors: Randall Alley, Thousand Oaks, CA (US); Adam Soss, Winnetka, CA (US); Dustin Bouch, Newport Beach, CA (US)

(73) Assignee: Otto Bock Healthcare IP GmbH & Co. KG, Duderstadt (DE)

( * ) Notice: Subject to any disclaimer, the term of this patent is extended or adjusted under 35 U.S.C. 154(b) by 256 days.

(21) Appl. No.: 11/168,956

(22) Filed: Jun. 28, 2005

(65) Prior Publication Data

US 2006/0289069 A1   Dec. 28, 2006

(51) Int. Cl.
 *F16K 15/00* (2006.01)
(52) U.S. Cl. .................. 137/543; 137/540; 285/317; 285/320; 623/33

(58) Field of Classification Search .................. 137/269, 137/540, 542, 543; 285/317, 320, 321; 623/33, 623/34, 35, 36, 37
See application file for complete search history.

(56) References Cited

U.S. PATENT DOCUMENTS

| | | | | |
|---|---|---|---|---|
| 4,564,365 A | * | 1/1986 | Winer et al. ................... 623/27 |
| 5,139,523 A | * | 8/1992 | Paton et al. ................... 623/37 |
| 5,490,537 A | * | 2/1996 | Hill ........................ 137/315.42 |
| 5,702,489 A | * | 12/1997 | Slemker ....................... 623/34 |
| 5,728,170 A | * | 3/1998 | Becker et al. .................. 623/37 |
| 6,063,125 A | | 5/2000 | Arbogast et al. |
| 6,079,445 A | * | 6/2000 | Huang .................... 137/614.04 |
| 6,287,345 B1 | | 9/2001 | Stemker et al. |
| 6,440,173 B1 | * | 8/2002 | Meyer .......................... 623/36 |

* cited by examiner

*Primary Examiner*—Kevin L Lee
(74) *Attorney, Agent, or Firm*—Faegre & Benson, LLP

(57) ABSTRACT

A valve assembly having a base and a removable latched insert that separately contains a valve piece. The valve piece is resiliently supported to abut a seal fitted to the insert. The insert is restrained to the base with a pair of resiliently biased latch arms that radiate from the insert. Flanges at the latch arms are resiliently biased to flex and grip the base as the insert is pushed into the base. Insert removal is effected with the release of the latch arms and a lifting of the latch arms.

26 Claims, 5 Drawing Sheets

LATCHED VALVE ASSEMBLY

FIELD OF THE INVENTION

The present invention relates to check valves and in particular to a latched valve used to maintain a preferred suspension pressure at a prosthetic socket or interface between a limb and a prosthesis, among other applications.

BACKGROUND OF THE INVENTION

The maintenance of a negative pressure or suction in a prosthetic socket or at a related interface to thereby facilitate a desired limb suspension is typically achieved through the use of an expulsion-type check valve (e.g. auto, manual or both). Such valves are typically configured to provide a threaded base or seat. The base, in turn, normally supports a threaded valve insert that is configured to ensure a proper airtight seal.

Proper placement of the valve insert relative to the base requires a high degree of dexterity and hand-eye coordination, especially when used in a prosthetic limb. That is, most typically the valve base is located at the most distal aspect of a limb socket. The base is typically thermoformed or laminated into the socket. Such a location can be difficult to see, but can also present an awkward relative alignment angle to mount or detach the valve insert.

Because the valve threads, which exhibit a relatively fine pitch, have to line up perfectly in order for the valve insert to be set properly, the combination of poor visibility and high demands for physical dexterity typically result in difficult donning situations for individuals with sound hands and fingers. Removal of the valve can present similar challenges, as the quality of the seal is often related to how tight the insert has been screwed into the valve base. A significant amount of friction can result from overzealous tightening of the valve insert, making it extremely difficult to remove.

For individuals with an involved upper extremity or extremities (e.g. injured, deformed, diseased or the result of insufficient congenital development), the insertion and/or removal of the valve insert from the valve seat can prove impossible. This circumstance is particularly onerous for the debilitated user who has to periodically self-adjust the limb.

The foregoing difficulties have been overcome with the present valve assembly, which provides a base that is adapted to receive a mating, latched insert. The valve assembly at the coupling junction between the base and insert is particularly constructed to provide for a latched connection. The interconnection provides a sliding, sealed valve insert piece that is respectively pushed or pulled from the seat or base during mounting and removal. The connection is maintained or broken with cooperating latch arms that assure proper insert retention.

SUMMARY OF THE INVENTION

It is a primary object of the present invention to provide a threadless valve assembly wherein a valve base or seat supports a mating, latched insert that supports a valve piece.

It is a further object of the invention to provide a valve assembly having a base containing a bore that accepts a slide mounted latching insert.

It is a further object of the invention to provide a valve assembly wherein an O'ring seals a valve insert within a seat bore.

It is a further object of the invention to provide a resiliently biased valve piece that is sealed within the valve insert.

It is a further object of the invention to provide a latched interconnection between the valve base or seat and the latched insert.

The foregoing objects are achieved in a presently preferred construction of the invention and valve assembly, which includes a threadless valve base and a threadless valve insert. The threadless insert is pushed into the valve base by hand or using a tool or other appliance that imparts sufficient pressure on the valve insert to overcome an internal resilient tension and seal friction.

The valve base and valve insert include overlapping, annular flange surfaces. An O'ring seals the insert within the base. A concentric, resiliently biased valve piece is retained in the insert with a second O'ring. Resiliently biased latch arms are mounted to the insert and located to pivot during insert insertion and extraction. Flanged latch surfaces at the arms flex outward during insertion and spring back to a concentric, restraining alignment with the base upon traversing an interconnecting annular flange at the base.

During insert removal, portions of the latch arms are depressed and pivoted to disconnect the arms from the base. The insert can then be removed, which action is facilitated if the insert is independently biased with other resilient devices (e.g. springs) fitted between the insert and base.

Although two latch arms are symmetrically arranged to the present base, a single latch arm or other arrangements of arms can be used. A plunger-type valve piece is used to allow auto or manual expulsion of air or other gas or liquid from the limb socket, although other types and mountings of the valve piece can also be adapted to the insert. Similarly, the valve piece might be latched to the insert in a related manner with latch arms or other threadless restraints. Although the present valve assembly finds particular application with prosthetic limbs, it is to be appreciated the valve might be used in other applications.

Still other objects, advantages and constructions of the present invention, among various considered improvements and modifications, will become apparent from the detailed description provided hereinafter. It should be understood that the detailed description and specific examples, while indicating a presently preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein similar reference callouts are used at the various figures, and wherein.

DETAILED DESCRIPTION OF THE PREFERRED EMBODIMENTS

The following description of the preferred embodiment is merely exemplary in nature and is in no way intended to limit the invention, its application, or uses. For purposes of clarity, the same reference numbers are used throughout the drawings to identify similar components.

Figure 1:
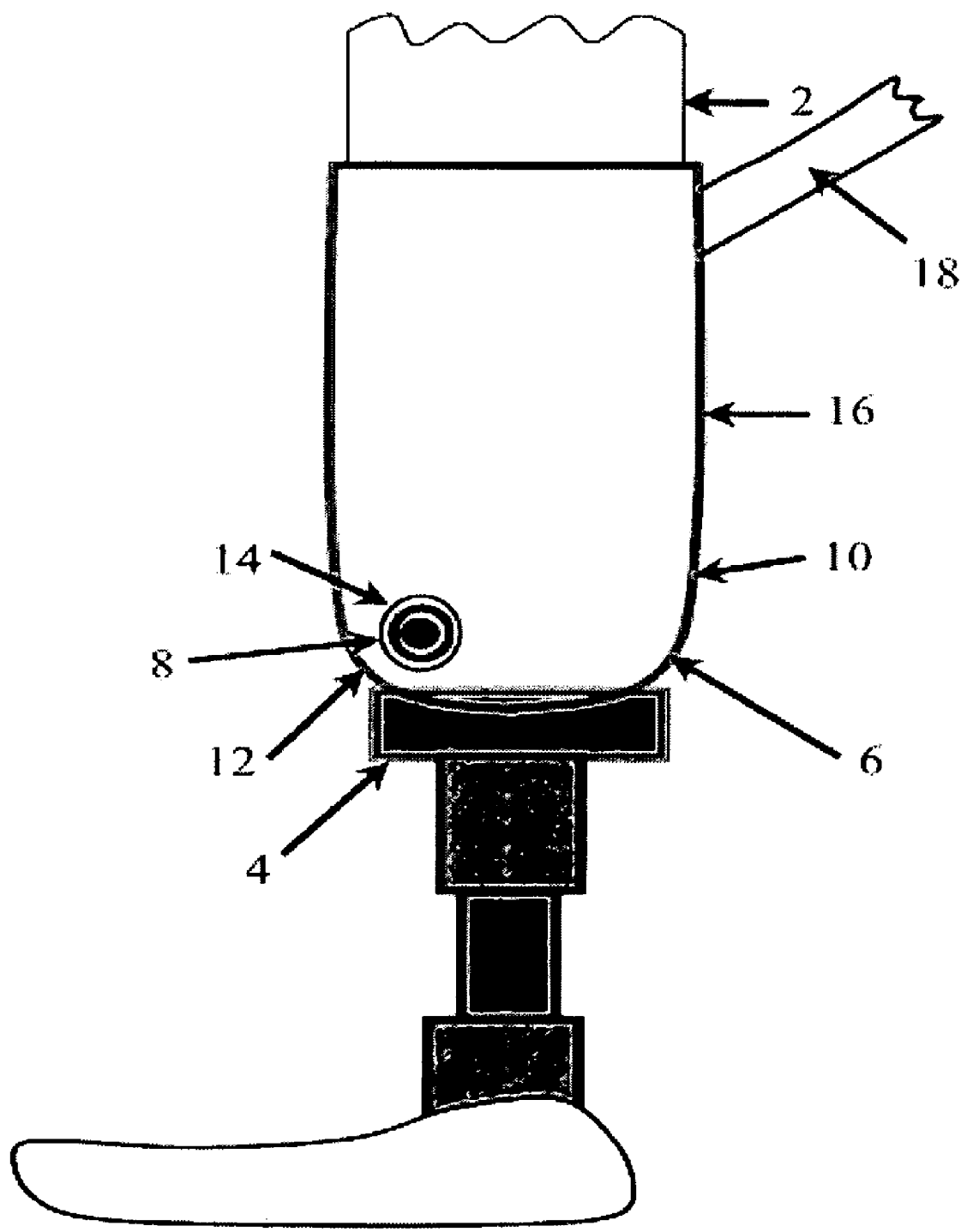
FIG. 1 shows a perspective view to a prosthetic limb that has been adapted to include one construction of a push valve assembly of the invention.

Referring to FIG. 1 a view is shown to a coupling between a limb 2 (e.g. a leg or arm) and a suitable prosthetic appliance 4. A cutaway view is shown to a limb socket 6 at the appliance 4 and where a valve 8 constructed in accord with the subject invention is shown. The valve 8 is fitted to a socket assembly 10 that is used at the interface between the appliance 4 and an extremity of the user's limb 2. The valve 8 is mounted to a socket piece 12 that is shaped to mate with a surgically prepared distal end of the limb extremity. A valve base 14 is typically thermoformed or laminated into the socket piece 12.

A collar or harness 16 is formed to contain the socket piece 12 and shelter the distal end of the extremity. Collar 16 has suitable padding and/or has straps 18 provided to enhance the durability of the attachment.

Depending upon the limb and application, a principal concern is to maintain a limb to prosthesis connection that provides maximum flexibility without causing limb ulceration. Various interfaces have been developed that use padding materials such as foams, plastics, polyester and acrylic resins etc. Interfaces that incorporate air, gas or liquid buffers or cushions or combinations thereof are also frequently used. It is with respect to prosthetic devices that use gas and/or liquid buffer materials that the valve 8 of the invention finds particular application.

The valve 8 is particularly used at included ports to allow the filling of the socket piece 12 with a suitable gas or liquid interface material between the socket piece 12 and limb extremity. The valve 8 also serves as a check valve to prevent the uncontrolled expulsion of the interface material.

Figure 2:
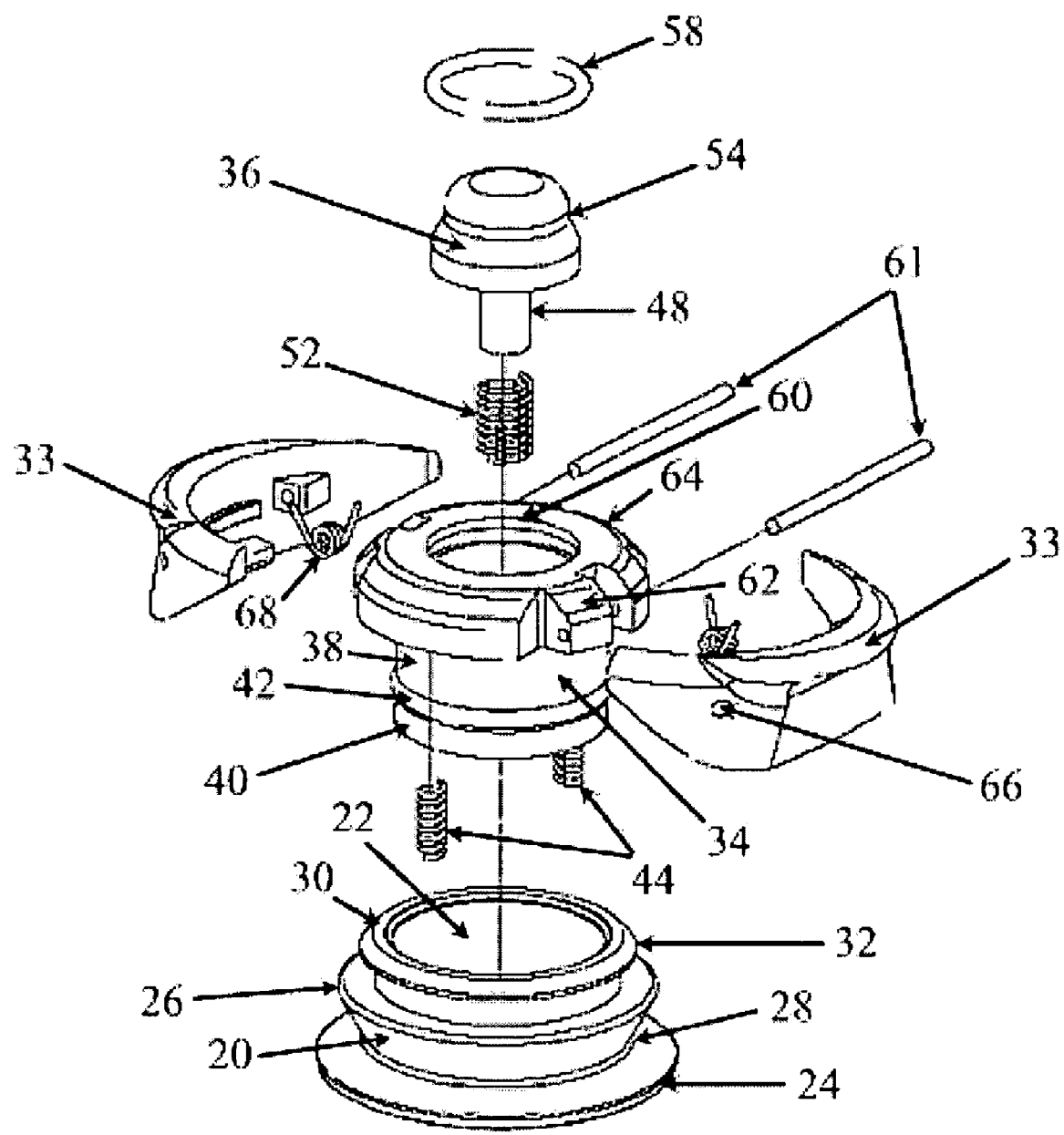
FIG. 2 shows an exploded drawing to the foregoing push valve assembly.

With attention to FIG. 2, the valve 8 is shown in exploded assembly. The valve 8 includes a base 20 that is designed to exhibit a suitable geometric configuration adapted to a preferred mounting of the valve 8. Presently, the base is generally cylindrical in shape, although could exhibit a hexagonal, octagonal or other shape.

A bore 22 longitudinally extends through the base 20. A ringed flange 24 projects from the base 8 and can be laminated to or thermoformed in a socket piece 12 with a variety of suitable adhesives and tapes. The diameter of the flange 24 can be varied as desired.

An adjoining tapered flange surface 26 is also provided that forms a "V", "U" or other suitably shaped groove 28 relative to the flange 24. The groove 28 accommodates valve retention within a thermoformed mounting. Suitable grooves, ridges, knurling or other types of projections and the like can be provided at the surface 26 and groove 28 to facilitate retention to the appliance 4.

Figure 3:
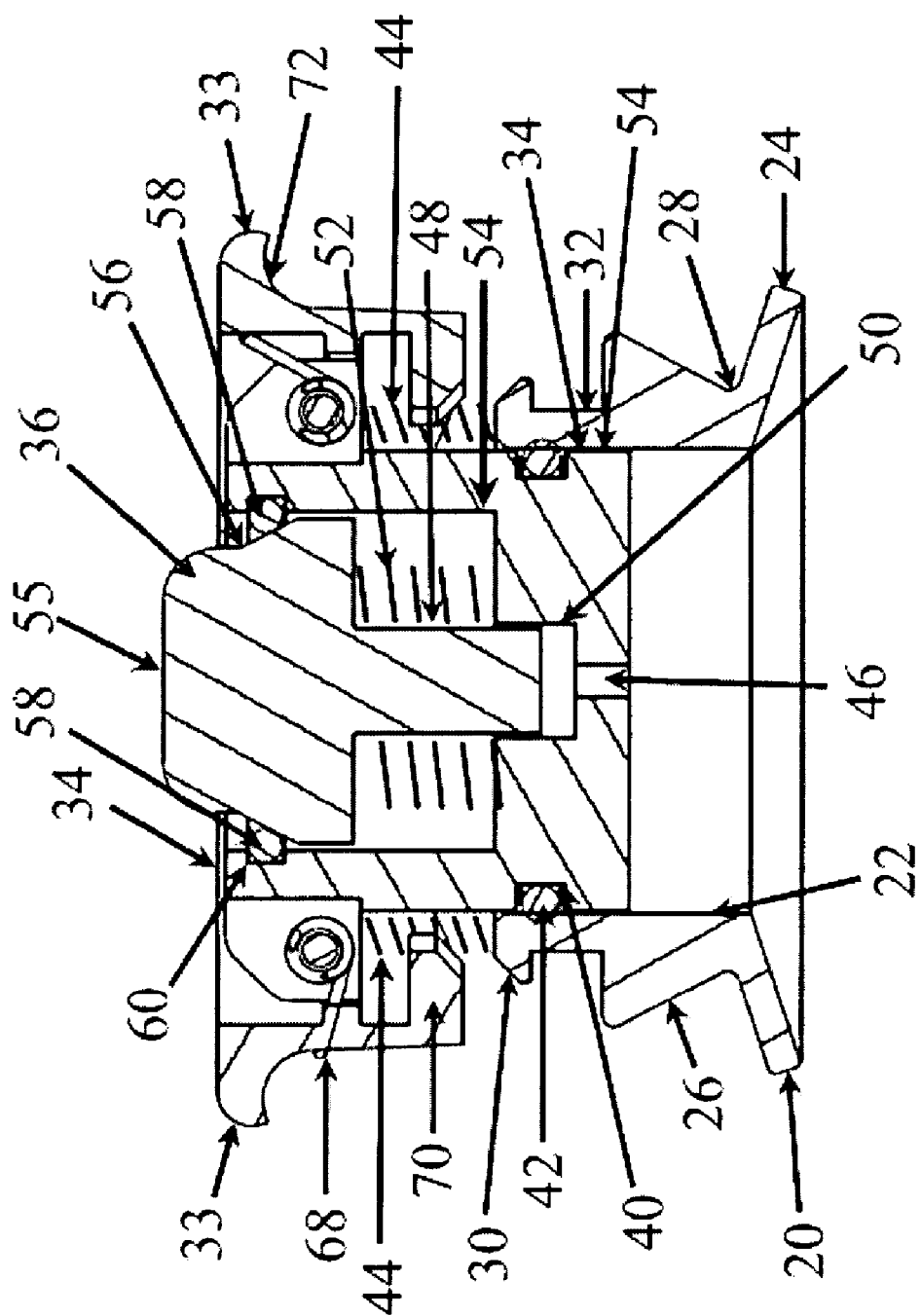
FIG. 3 shows a cross section drawing to the valve assembly at an initial insertion position or just prior to complete removal of the insert from the valve base.
Figure 4:
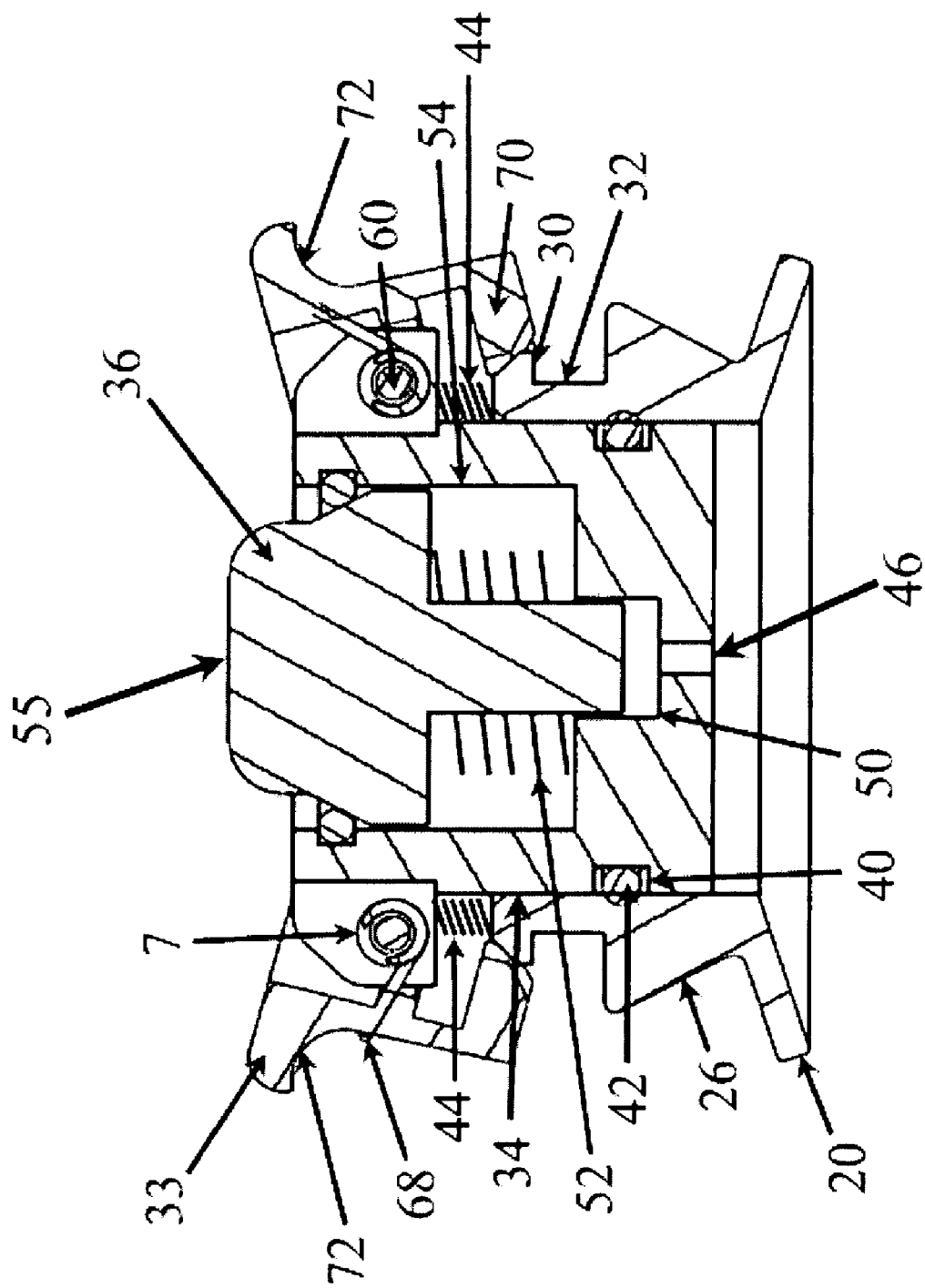
FIG. 4 shows a cross section drawing to the valve assembly with the latch arms squeezed toward one another in preparation for full insertion or removal.
Figure 5:
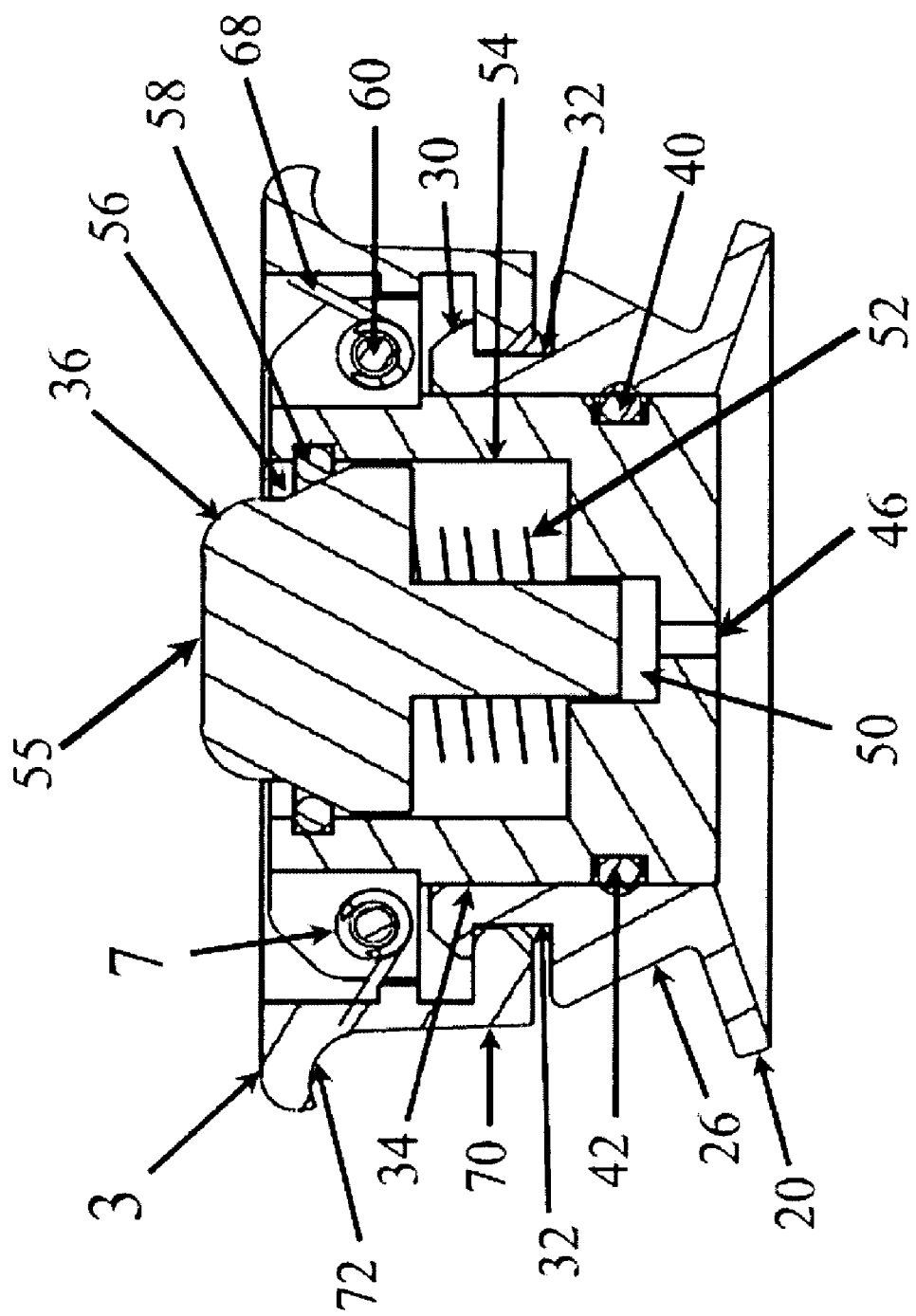
FIG. 5 shows a cross section drawing to the valve assembly with the latch arms latched closed to contain a concentric expulsion valve piece contained within the valve base.

A third flanged surface 30 is provided that defines a groove 32 relative to the outermost portion of the flange 26. The groove 32 contains a pair of latch arms 33 that pivot from an associated valve insert 34 to secure the insert 34 and a valve piece 36 at the insert to the bore 22. The details of the mounting of the insert 34 and valve piece 36 are more apparent from the following description with respect to the section views at FIGS. 3, 4 and 5. The flange surfaces 26 and 30 are preferably circularly continuous although can be segmented into a number of discontinuous sections.

The insert 34 provides a generally cylindrical stem piece or body 38 that is sized to closely mate with the diameter of the bore 22. An annular groove 40 contains an O'ring seal 42. The seal 42 prevents the migration of a gas or liquid contained within the socket piece 12 through the bore 22 and past the insert 34. A pair of springs 44 depend from the body 38 and normally bias the insert 34 to an elevated condition. Although the base 20 and insert 34 are shown in cylindrical shapes, other shapes or combinations of shapes can be adapted as desired. The insert 34 might also be constructed to index to a preferred alignment with the base 20. The springs 44 are supported at their top by recessed holes that receive and maintain the alignment of each spring 44 and are supported at their base by resting on the top edge of the valve base.

A port 46 is aligned to the longitudinal center of the body 38. A stem 48 of the valve piece 36 is separately restrained to the insert 34 at a bore 50 to control liquid or gas flow through the port 46 and bore 50. A spring 52 is supported about the stem 48 in a bore 54 and biases a circular, tapered surface 56 at a head 55 of the valve piece 36 to seal against an O'ring 58 contained at a groove 60 within the bore 54.

The valve piece 36 thus acts as a check valve and prevents flow through the bores 54, 50 and port 46, unless the valve piece 36 is depressed from contact with the O'ring seal 58. It is to be appreciated a variety of other resilient devices and materials can be used to bias the valve piece 36. Similarly, different seat/seal arrangements can be configured between the valve piece 36 and bore 54 to control flow through the bores 46, 50 and 54. The valve piece 36 may also be mounted such that it is normally depressed against the port 46 versus being raised above the port 46, such as with the aid of a snap ring (not shown) and spring 52 mounted to bias the stem 48 to engage the port 46.

The insert 34 is restrained to the base 20 with the latch arms 33 which are mounted to pivot about pivot pins 61. The pins 61 mount through segmented portions 62 of a flange 64 that radiates from the sidewalls of the insert 34 and nest within aligned bores 66 in the arms 33. A torsion spring 68 is fitted around each pin 60 and between the flange 64 and arms 33. The ends of the springs 68 are retained to induce flanges 70 in the arms 33 to pivot inward. Thus, the flanges 70 are restrained beneath the flange 30 in the base 20 and secured to the groove 32, once the insert 34 is fully seated within the base 20. Although two latch arms 33 are presently used, a single arm or additional arms might alternatively be incorporated into the assembly 8. The flanges 70 might also be restrained to depressions or projections In the latter regard, attention is drawn to FIGS. 3, 4 and 5 and wherein the flanges 70 at the arms 33 are respectively shown in a depressed condition at FIG. 3, a partially flexed condition at FIG. 4 and a seated condition at FIG. 5. During normal mounting, the insert 34 is merely aligned to the base 20 and the tapers at the flanges 70 and 30 induce the flange arms 33 to pivot outward, reference FIGS. 3 and 4. Once the insert 34 is pushed past the flange 30, the flanges 70 spring inward and are captured in the groove 32, reference FIG. 5.

The valve piece 36 mounts merely by suitably lubricating the piece 36 and depressing it and the spring 52 into the bore 54. Removal of the insert 34 is effected by manually lifting up on the finger depressions 72. A typical user of a prosthesis 4 having an air or liquid interface material is thereby now able to readily fit and make suitable adjustments to enhance the fit and comfort of the prosthesis.

The first O'ring 42 may be located in the base or in the insert.

From the foregoing, it is to be appreciated the described construction of the complete valve assembly 8 is merely exemplary of a presently preferred valve. From the suggested modifications and others that might become apparent to those skilled in the art, it also is to be appreciated that the invention can be implemented in still other configurations. Still further, selected portions of the assembly might also be adapted into other valve assemblies. The scope of the invention should therefore not be construed merely to the foregoing description, but rather should be construed within the broader scope of the following claims.

What is claimed is:

1. A valve comprising:
    a) a base having i) a body through which a bore extends, ii) a mounting flange, wherein said mounting flange radiates from the base body, and iii) a depression displaced from said flange;
    b) a first seal and a second seal;
    c) an insert having a body adapted to mount in the bore of said base and engage said first seal with said first seal having a portion between said insert and said base, wherein the insert body includes a flow bore and wherein an arm having a flanged surface is mounted to move relative to the insert body such that the flanged surface mates with the depression at said body, whereby said insert can be inserted, restrained and withdrawn from said base upon pivoting said arm relative thereto a predetermined distance; and
    d) a valve piece having a stem adapted to mount in the bore of said insert and wherein a surface of said valve piece mates in sealing engagement with the second seal having a portion disposed between said insert at said flow bore and said valve piece.

2. A valve as set forth in claim 1 including a plurality of springs mounted to bias said insert in the bore of the base body and said valve piece in the bore of the insert body.

3. A valve as set forth in claim 1 including a spring mounted to resiliently bias said arm to pivot as said insert is mounted in the bore of said base and return said arm to a retention condition once said flanged surface is aligned to said depression.

4. A valve as set forth in claim 1 wherein said depression comprises a groove and including first and second arms having flanged surfaces that engage said groove.

5. A valve as set forth in claim 4 wherein said first and second arms are resiliently biased to flex and return to a retention condition when the flanged surfaces of said first and second arms engage said groove.

6. A valve as set forth in claim 1 wherein said first and second seals comprise O'rings.

7. A valve as set forth in claim 1 wherein said mounting flange is annular and exhibits a diameter greater than a diameter of the base body.

8. A valve as set forth in claim 7 wherein the base body includes an annular groove and wherein said insert includes first and second resiliently biased arms which are biased to flexibly pivot and return to a retention condition when flanged surfaces of said first and second arms engage said groove and thereby restrain said insert to said body.

9. A valve as set forth in claim 8 wherein said insert includes surfaces adapted for hand manipulation of said first and second arms.

10. A valve as set forth in claim 1 wherein the first seal and second seal are supported by the insert.

11. A valve comprising:
    a) a base having i) a cylindrical body through which a bore extends, ii) an annular mounting flange which radiates from the base, and iii) an annular groove displaced from said mounting flange;
    b) a first O'ring seal and a second O'ring seal;
    c) an insert having a body adapted to mount in the bore of said base and engage said first O'ring seal with said first O'ring seal having a portion between said insert and said base, wherein the insert body includes a flow bore and wherein an arm having a flanged surface is resiliently biased to move relative to the insert body such that the flanged surface mates with the groove at the base body, whereby said insert can be inserted, restrained and withdrawn from said base upon moving said arm relative thereto a predetermined distance; and
    d) a valve piece having a stem adapted to mount in the bore of said insert and wherein a surface of said valve piece mates in sealing engagement with the second O'ring seal having a portion disposed between said insert at said flow bore and said valve piece.

12. A valve as set forth in claim 11 wherein said insert includes first and second resiliently biased arms each having a flanged surface and which first and second arms are biased to resiliently pivot and return to a retention condition when the flanged surfaces engage said groove and thereby restrain said insert to said body.

13. A valve as set forth in claim 11 including a spring for biasing said valve piece into abutment with said second O'ring.

14. A valve as set forth in claim 11 including first and second firms, each having a flanged surface that is adapted to mate with said groove, and including a plurality of springs for pivotally biasing said first and second arms.

15. A valve as set forth in claim 11 including a resilient member for biasing said insert in said body.

16. A valve as set forth in claim 15 including a plurality of resilient members biasing said insert to a retention condition in said body and biasing said valve piece into sealed engagement with said O'ring seal.

17. A valve as set forth in claim 12 wherein the first O'ring seal and second O'ring seal are supported by the insert.

18. A valve comprising:
    a) a base having i) a cylindrical body through which a bore extends, ii) a first sealing surface located within said bore, and iii) a flanged mounting surface;
    b) an insert having a body adapted to mount in the bore of said base and engage said first sealing surface, wherein the insert body includes a flow bore having a second sealing surface within the flow bore, and wherein an arm having a flanged surface is resiliently biased to move relative to the insert body such that the flanged surface mates with the flanged mounting surface at the base body, whereby said insert can be inserted, restrained and withdrawn from said base upon appropriately manipulating said arm; and
    c) a valve piece having a stem adapted to mount in the bore of said insert and wherein a surface of said valve piece mates in sealing engagement with the second sealing surface.

19. A valve as set forth in claim 18 including a plurality of resilient members biasing said insert to a retention condition in said body and biasing said valve piece into sealed engagement with said second sealing surface.

20. A valve as set forth in claim 18 including a plurality of resilient members biasing said insert to a retention condition in said body and biasing said valve piece into sealed engagement with an O'ring that defines said second sealing surface.

21. A valve as set forth in claim 20 including first and second arms, each having a flanged surface that is adapted to mate with a groove in the insert body, and including a plurality of springs for pivotally biasing said first and second arms.

22. A valve as set forth in claim 18 including first and second arms, each having a flanged surface that is adapted to mate with a groove in the insert body, and including a plurality of springs for pivotally biasing said first and second arms.

23. An expulsion valve for a prosthetic device, the valve comprising:
   a) a valve base defining an air passage and receptacle portion, the air passage communicating with the receptacle portion;
   b) a threadless valve insert for fitting within the receptacle portion for sealing the air passage when held in a seated position; and
   c) a resilient device on the valve insert and having an actuator, wherein the resilient device is normally biased into a locked position with the valve base when the valve insert is in the seated position, wherein pressing on the actuator acts against the bias of the resilient device to disengage from the locked position and enable removal of the valve insert from the seated position.

24. The expulsion valve of claim 23 wherein the resilient device comprises two torsion springs and the actuator comprises two levers, each having thereon one of the two torsion springs, and each pivotably mounted on the valve insert.

25. The expulsion valve of claim 23 wherein the valve insert further comprises a check valve.

26. The expulsion valve of claim 24 wherein there is an O-ring mounted on the check valve for engaging and sealing a channel on the insert valve for communicating with the passage.

* * * * *